(12) United States Patent
El Sabahy et al.

(10) Patent No.: US 11,504,341 B2
(45) Date of Patent: Nov. 22, 2022

(54) NANOTECHNOLOGY-BASED HEMOSTATIC DRESSINGS

(71) Applicant: Egy-Nano Pharma, LP, Assiut (EG)

(72) Inventors: Mahmoud Fahmy Ali El Sabahy, College Station, TX (US); Mostafa Ahmad Mostafa Mohammad Hamad, Assiut (EG)

(73) Assignee: EGY-NANO PHARMA, LP, Assiut (EG)

( * ) Notice: Subject to any disclaimer, the term of this patent is extended or adjusted under 35 U.S.C. 154(b) by 71 days.

(21) Appl. No.: 16/322,379

(22) PCT Filed: Sep. 26, 2017

(86) PCT No.: PCT/US2017/053472
§ 371 (c)(1),
(2) Date: Jan. 31, 2019

(87) PCT Pub. No.: WO2018/080692
PCT Pub. Date: May 3, 2018

(65) Prior Publication Data
US 2020/0179297 A1 Jun. 11, 2020

Related U.S. Application Data

(60) Provisional application No. 62/413,823, filed on Oct. 27, 2016.

(51) Int. Cl.
| | |
|---|---|
| *A61K 9/70* | (2006.01) |
| *A61K 31/717* | (2006.01) |
| *A61P 7/04* | (2006.01) |
| *A61K 31/722* | (2006.01) |
| *A61K 35/02* | (2015.01) |
| *A61K 38/39* | (2006.01) |

(52) U.S. Cl.
CPC .......... *A61K 9/7007* (2013.01); *A61K 9/7015* (2013.01); *A61K 31/717* (2013.01); *A61K 31/722* (2013.01); *A61K 35/02* (2013.01); *A61K 38/39* (2013.01); *A61P 7/04* (2018.01)

(58) Field of Classification Search
None
See application file for complete search history.

(56) References Cited

U.S. PATENT DOCUMENTS

| | | | | |
|---|---|---|---|---|
| 7,910,135 | B2 * | 3/2011 | St. John | ........... A61P 27/02 424/501 |
| 8,383,148 | B2 | 2/2013 | Huey et al. | |
| 11,007,218 | B2 * | 5/2021 | Basadonna | ....... A61F 13/00034 |
| 2006/0013863 | A1 * | 1/2006 | Shalaby | ........... A61L 31/06 524/556 |
| 2007/0154510 | A1 | 7/2007 | Wilcher et al. | |
| 2008/0199539 | A1 | 8/2008 | Baker et al. | |
| 2010/0216211 | A1 | 8/2010 | Shauer et al. | |
| 2010/0303922 | A1 * | 12/2010 | Yuk | ........... C08L 71/02 424/501 |
| 2011/0311632 | A1 | 12/2011 | Roorda et al. | |
| 2013/0344131 | A1 * | 12/2013 | Lo | ........... A61L 15/28 424/447 |
| 2014/0255336 | A1 | 9/2014 | Kudela et al. | |
| 2015/0283286 | A1 | 10/2015 | Eastwood et al. | |
| 2016/0346239 | A1 * | 12/2016 | Korobov | ........... A61K 47/26 |

FOREIGN PATENT DOCUMENTS

| | | | |
|---|---|---|---|
| CN | 103505758 | * 2/2015 | |
| WO | WO-2014135689 A2 | * 9/2014 | ........... A61K 9/1623 |
| WO | WO 2015/140563 | * 9/2015 | |
| WO | 2016133483 A1 | 8/2016 | |

OTHER PUBLICATIONS

Ryu, Ji Hyun et al., "Catechol-Functionalized Chitosan/Pluronic Hydrogels for Tissue C41 Adhesives and Hemostatic Materials", ACS Publications, May 21, 2011, pp. 2653-2659.
Rowe, Aaron, "Nanoparticles Help Gauze Stop Gushing Wounds", wired.com, Apr. 24, 2008, pp. 1-3. (last visited Jan. 3, 2019).
International Search Report and Written Opinion dated Dec. 7, 2017 for Application No. PCT/US2017/053472.
Wang et al, "A New, Pluronic-based, Bone Hemostatic Agent That Does Not Impair Osteogenesis", Neurosurgery, Williams & Wilkins, Baltimore, MD, US vol. 49, No. 4, Oct. 1, 2001, pp. 962-968.
Karahaliloglu et al, "Active nano/microbilayer hemostatic agents for diabetic rat bleeding model: Hemostatic Agents for Diagetic Rat Bleeding Model", Journal of Biomedical materials Research Part B: Applied Biomaterials, vol. 105, No. 6, Apr. 29, 2016, pp. 1573-1585.
Laurenti et al., "Enhanced pro-coagulant hemostatic agents based on nanometric zeolites", Microporous and Mesopourous Materials, vol. 239, 263-271.
Ilinskaya et al., "Nanoparticles and the blood coagulation system. Part I: benefits of nanotechnology", Nanomedicine, vol. 8, No. 5, May 1, 2013, pp. 773-784.
European Office Action dated Jan. 20, 2021 for Application No. 17781280.7.
European Office Action dated Apr. 21, 2020 for Application No. 17781280.7.

* cited by examiner

*Primary Examiner* — Tigabu Kassa
(74) *Attorney, Agent, or Firm* — Patterson + Sheridan, LLP

(57) ABSTRACT

Hemostatic compositions including a combination of more than one hemostatic agent, and devices coated or impregnated therewith, have been developed. Nanotechnology yields hemostatic agents with large surface areas thereof, thereby increasing the hemostatic properties of the device to which they are applied. By combining more than one hemostatic agent and utilizing one or more different nanotechnology approaches to enhance the surface areas thereof, the capability of the dressing to stop bleeding is improved via more than one mechanism, and thus provides better hemostasis.

16 Claims, 3 Drawing Sheets

NANOTECHNOLOGY-BASED HEMOSTATIC DRESSINGS

CROSS-REFERENCE TO RELATED APPLICATIONS

This application claims benefit to International Application No. PCT/US2017/053472, filed Sep. 26, 2017, the entirety of which is herein incorporated by reference, which claims benefit of U.S. Provisional Patent Application No. 62/413,823, filed Oct. 27, 2016, the entirety of which is herein incorporated by reference.

FIELD

The present disclosure generally relates to hemostatic dressings with high efficiency in controlling bleeding, and more particularly to a combination of several hemostatic agents, each designed to possess a high surface area, with the aid of different nanotechnology approaches, and their use in preparing hemostatic dressings.

BACKGROUND

Bleeding is a major cause of pre-hospital deaths, in particular when it cannot be controlled in the first few hours. Persistent bleeding following interventional procedures is a common complication and may cause prolonged hospitalization. Persistent bleeding after injury or interventional procedures is an important cause of morbidity. Hemostatic dressings are regularly applied early after hemorrhage, irrespective of the cause, to reduce blood loss, until the patients receive the necessary medical care in the appropriate health care units.

Currently, there are several hemostatic dressings that are either in the market or under development. QUIKCLOT COMBAT GAUZE® is a hemostatic dressing used on the battlefield. The active hemostatic agent is kaolin which is aluminum silicate that activates the intrinsic pathway of coagulation and concentrates clotting factors through the rapid absorption of the water content of blood at the bleeding site. It is carried by all branches of the U.S. military to control life-threatening hemorrhage. No adverse reactions have been related to the use of QUIKCLOT COMBAT GAUZE®. QUIKCLOT COMBAT GAUZE® is a soft and sterile 7.6 cm by 3.7 m rolled gauze impregnated with kaolin and individually wrapped in a foil pouch. It is indicated for temporary external control of traumatic bleeding to all wounds.

Other commercially available hemostatic dressings include CELOX™ GAUZE AND HEMCON® which both depend on including chitosan as the hemostatic agent. Chitosan is a naturally occurring biodegradable polysaccharide which breaks down in the body into glucosamine and N-acetyl glucosamine. It is obtained through the partial deacetylation of chitin in the shells of shrimp and other crustaceans. Chitosan is extensively used in food and pharmaceutical industries. It has intrinsic bioadhesive and antimicrobial properties and it induces hemostasis via electrostatic interaction with the negatively charged cell membranes of RBCs, and, thus strongly adhering to and sealing the bleeding site.

Although commercially available hemostatic agents can be effective in stopping the bleeding of mild hemorrhages, improved hemostatic dressings are needed to treat severe bleeding or bleeding in individuals with special circumstances (e.g. diabetes, hemophilia, battlefield, etc.).

Therefore, it is an object of the present disclosure to provide a different hemostatic dressing based on nanotechnology with improved efficiency in controlling bleeding and methods of use thereof.

SUMMARY

Hemostatic compositions including a combination of more than one hemostatic agent, and devices coated or impregnated therewith, have been developed. Nanotechnology yields hemostatic agents with large surface areas thereof, thereby increasing the hemostatic properties of the device to which they are applied. By combining more than one hemostatic agent and utilizing one or more different nanotechnology approaches to enhance the surface areas thereof, the capability of the dressing to stop bleeding is improved via more than one mechanism, and thus provides better hemostasis. The examples below show that the disclosed hemostatic devices effectively controlled bleeding and improved hemostasis and survival rates in the tested animals compared to a commercially available control, and were very effective when applied clinically in humans.

Typically, a hemostatic composition includes two or more hemostatic agents in combination with a surfactant in an effective amount to reduce bleeding and increase clotting, or a combination thereof when applied to a carrier or device and contacted with a wound or hemorrhage on a subject. In some embodiments, at least one of the hemostatic agents is in the form of particles, fibers, or another structure that is smaller than 1 micron (i.e., a nanostructure). Exemplary hemostatic agents include, but are not limited to, kaolin, chitosan, oxidized regenerated cellulose and collagen. Preferred compositions include chitosan, for example, chitosan in the form of nanofibers formed by electrospinning. Preferred compositions also include kaolin.

The surfactant is typically present in the composition in an effective amount to increase stability, enhance disbursement, increase the surface area, or a combination thereof of one or more hemostatic agents. Exemplary surfactants include POLOXAMERS® (nonionic triblock copolymers composed of a central hydrophobic chain of polyoxypropylene flanked by two hydrophilic chains of polyoxyethylene) and glycerol.

Carriers and devices such as sponges, gauzes, bandages, swabs, sprays, aerosols, gels, cements, compression bandages, pillows, and sleeves coated, impregnated, or otherwise contacted with the hemostatic composition are also provided. In some embodiments, the total amount of hemostatic agents is in the range of 5-50% of the total weight of the device or carrier. The total amount of surfactant can be in the range of 0.1-5% of the total weight of the device or carrier. The carrier or device can be degradable or non-degradable, absorbable or non-absorbable.

Methods of treating a subject in need thereof are also provided. The methods typically include contacting the carrier or device to a bleeding external or internal wound or hemorrhage site of the subject for a time sufficient to reduce bleeding, promote blood clot formation, or a combination thereof. In some embodiments, the bleeding is reduced to a greater degree, clotting is increased to a greater degree, or a combination thereof compared to using, for the same period of time, a comparable device prepared without utilizing one or more of the disclosed nanotechnology approaches (e.g., lacking a surfactant, lacking a nanoparticularized hemostatic agent, or a combination thereof, in the hemostatic composition).

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, for the disclosure may admit to other equally effective embodiments.

DETAILED DESCRIPTION

Figure 1:
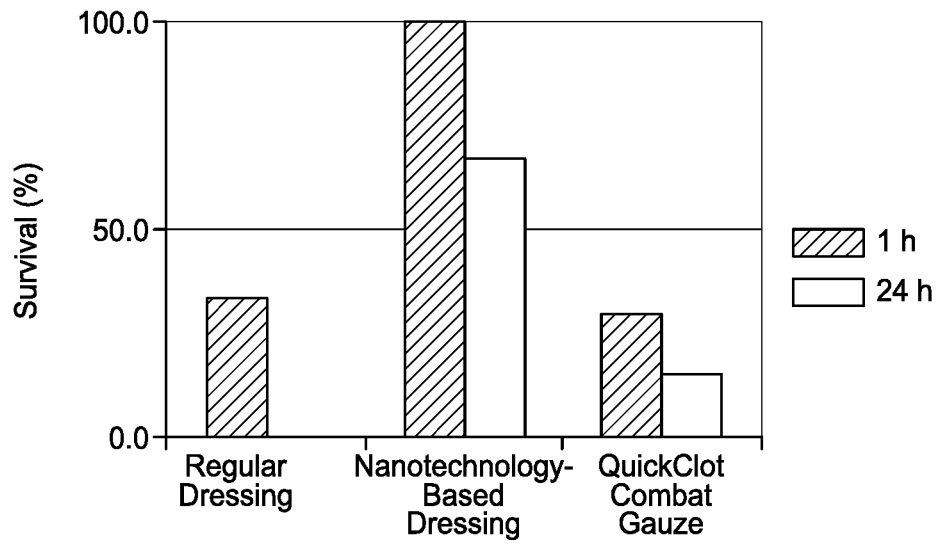
FIG. 1 is a graph displaying the percentage of survival of animals, 1-h and 24-h, after cutting their femoral arteries and veins. Regular dressings, nanotechnology-based dressing, or QUIKCLOT® were applied immediately after injury with immediate compression for 3 min.

As used herein, "hemostatic agent" refers to a material aid in controlling the bleeding, irrespective of its mechanism of action.

As used herein, "nanotechnology approach" is a strategy utilized to increase the surface area of the hemostatic agent. This includes designing the materials itself on the nanoscale range (at least at one dimension) or use of nanoparticles of different types to provide physical stability and/or assist in dispersing the hemostatic materials and/or increasing its surface area.

As used herein, "hemostasis" refers to control of the bleeding which might be from external sites, deep wounds, or resulted from surgical intervention or injury during the battlefield. It can also involve various types of tissues (e.g. liver, lung, spleen, heart, dental, etc.). It also refers to the pharmaceutical applications of these dressings either clinically in human or for veterinarian applications in animals.

I. Hemostatic Devices

Hemostatic compositions and devices prepared therewith typically include one or more hemostatic agents prepared using a nanotechnology approach to increase the surface area of the hemostatic agent. The hemostatic composition is applied onto and/or into a carrier or device to form a hemostatic device. Typically the hemostatic device includes two or more hemostatic agents. At least one, and preferably two of the hemostatic agents are applied to the device as part of a hemostatic composition. In some embodiments, the device is separately coated or impregnated with two or more hemostatic compositions that each includes one or more hemostatic agents.

A. Hemostatic Compositions

Hemostatic compositions typically include one, or preferably two or more hemostatic agents. In preferred embodiments, the composition also includes one or more surfactants. For example, in some embodiments the hemostatic composition is prepared by combining one or more hemostatic agents and one or more surfactants in an effective amount to increase stability of a hemostatic agent, enhance disbursement of a hemostatic agent, increase the surface area of a hemostatic agent, and/or the surface area covered or coating by the hemostatic agent, or a combination thereof. Additionally or alternatively, one or more of the hemostatic agents can be prepared in a nanoscale range in at least one dimension to increase its surface area. In some embodiments, nanotechnology approaches enhance the surface area of one or more of the utilized hemostatic devices (e.g., dressings).

In particularly preferred embodiments, the hemostatic composition includes chitosan, kaolin, and a PLURONIC® surfactant. Additional hemostatic agents and surfactants are discussed in more detail below.

1. Hemostatic Agents

The hemostatic composition typically includes two or more hemostatic agents. Hemostatic agents are usually granular, and can be film, gel, powder or fibers. In some embodiments, one or more of the hemostatic agents is in the form of, or otherwise includes particles, such as micro- or nanoparticles; fibers, such as micro- or nanofibers; or another micro- or nanostructures. The surfactant may also be in the form of a nanoparticle, for example, as a micelle.

It is important and has been empirically determined that the combined materials in the hemostatic composition do not interfere with each other, reduce the hemostatic effect of one another, and does not impact the physical stability of one another. If not combined in the proper way, either poor physical stability or hemostatic efficiency can be found.

Preferably one or more of the hemostatic agents has bioadhesive properties per se. This is beneficial to reduce the compression/application time required before leaving the dressing at the injury site.

The total amount of hemostatic agents is typically in the range of 5-50% of the total weight of the device or carrier (e.g., a dressing) onto or into which it is applied. The ratio of the combined hemostatic agents is in the range of 1-10:50 by weight.

a. Clays

The hemostatic agent can be a natural or modified clay. Exemplary clays include, but are not limited to, kaolin, kaolinite, bentonite, montmorillonite, palygorskite, saponite, and combinations thereof. Modified clays such as polyorganosilcate graft polymers may also be suitable. In a preferred embodiment, but the clay is kaolin. Kaolin used is a hydrated aluminum silicate that meets USP specifications, and is rich in aluminosilicate nanoparticles, which trigger blood clotting (Rowe, et al., "Nanoparticles help gauze stop gushing wounds," Wired.com, Apr. 24, 2008).

Where the layered clay exhibits a morphology having relatively less accessible surface area, it may be desirable to decrease the average particle size of the layered clay, e.g., to less than 1 micron to provide layered clay particles having an average particle size in the submicron (e.g., nanoparticle) range. See, e.g., U.S. Published Application No. 2008/0199539.

b. Chitosan

The hemostatic agent can be a chitosan. Chitosan, either medium—(190000-310000 Da, 75-85% deacetylation degree) or high—(310000-375000 Da, >75% deacetylation degree) molecular weights, can be used as acetate salts via combining the chitosan with acetic acid.

Electrospinning is one of the strategies which are utilized for producing chitosan nanofibers. For example, chitosan salt (acetate) solutions at different concentrations are prepared by dissolving chitosan powder of different molecular weights and acetylation degrees in acetic acid of varying strengths. Chitosan can be obtained from commercial suppliers with different molecular weights and degree of acylation.

Heating at 50° C. for 2 h is regularly utilized during the stirring, which continues overnight. After electrospinning, chitosan nanofibers are dried under vacuum overnight to remove acetic acid and water residues. Then, chitosan nanofibers are stored in a desiccator until characterization. Transmission electron microscopy is usually utilized to measure the average dimensions of the formed nanofibers.

Factors controlled to obtain fibers on the nanoscale include, molecular weight of chitosan, concentrations of the chitosan and acetic acid solutions, homogeneity and viscosity of chitosan solution, applied electric field, beading rate, the distance between collector and needle of the electrospinning instrument.

Preferred conditions to get chitosan nanofibers were: medium and high molecular weight chitosan, 1-10% chitosan dissolved in 3-10% acetic acid solution, applied voltage around 25 kV, flow rate around 0.4 mL/h, the distance between needle tip and the collector is 5-20 cm.

c. Other Hemostatic Agents

Alternatively, the hemostatic agent can be an oxidized regenerated cellulose or collagen.

2. Surface Active Agents

The hemostatic composition can include a surface active agent (also referred to as a surfactant). The surfactant can be utilized to form nanoparticles that stabilize hemostatic agents can increase stability of a hemostatic agent, enhance disbursement of a hemostatic agent, increase the surface area of a hemostatic agent, and/or the surface area covered or coating by the hemostatic agent, or a combination thereof. The total amount of the surface active agent in the dressing is typically 0.1-5% of the total weight of the device or carrier (e.g., a dressing) onto or into which it is applied.

The surface active agents utilized to form the nanoparticles are pharmaceutically acceptable and preferably approved by the United States Food and Drug Administration for human administration. Examples of preferred surfactants include, but are not limited to, a poloxamer such as PLURONICS® F-127 and PLURONICS® F-68, and glycerol.

The size of the fibers and the size of the nanoparticles used to stabilize the hemostatic agents (usually measured by dynamic light scattering and transmission electron microscopy) greatly influenced the hemostasis achieved after the application of the dressing on the wounds. The size of the fibers and nanoparticles is controlled during process. For example, chitosan can be prepared using a basic preparation of chitosan purchased with a defined molecular weight range. Fibers are preferably formed with at least one dimension of less than 500 nm.

The surface active agents are typically prepared as aqueous solution of varying percentages (1-30% by weight) and mixed with aqueous solution of the hemostatic agents (1-50% by weight), followed by agitation for few hours.

B. Carriers and Devices

The hemostatic composition is typically coated onto, inserted into, and/or otherwise applied to a carrier for application to a site that is bleeding or oozing in an effective amount to reduce bleeding in a subject in need thereof. The carrier is coated with hemostatic materials, excipients, and inert materials, which each may be part of the hemostatic composition or added to the carrier separately or independently. As discussed above, the carrier can be treated with two or more hemostatic compositions, each with one or more hemostatic agents. In some embodiments, the carrier is treated with a hemostatic composition, for example a composition including at least one hemostatic agent and surfactant, and separately treated with an additional hemostatic agent. The hemostatic agent is not applied directly to the injured tissue.

The carrier can be a device, for example, woven or non-woven gauze, or other degradable or non-degradable materials. Degradable carriers may be also utilized for hemostatic applications that require the dressing to be left in place, for example, in some surgical operations.

Exemplary carriers include, for example, sterile sponge, gauze, bandage, swab, spray, aerosol, gel, cement, compression bandage, pillow (e.g., to facilitate application to a head wound), sleeve (e.g., for covering a wound on a limb), and the like. In some embodiments, the device serves as a substrate for the hemostatic composition, where the hemostatic agent in the hemostatic composition can be adhered to the device. For example, the hemostatic composition can be provided on a blood-accessible surface of the device (e.g., as a surface coating), and/or within the device (e.g., permeating at least a portion of an absorbent material, such as gauze). It is to be understood that a "coating" is at least on the surface of the substrate to which it is applied, and may permeate beyond the surface, such as where the substrate is an absorbent material.

Different shapes of the device or dressing are available according to the application. Examples include but not limited to, long gauze for bleeding in accidents or surgery, small tampons for dental applications, small pieces for First Aid Kits, etc.

Method of coating the carrier with the hemostatic composition may be through impregnation of the carrier in a solution of the hemostatic composition (separately or combined) or spraying solution of the hemostatic composition and other ingredients (separately or combined) over the carrier. After preparation, hemostatic devices can be dried in air overnight or in oven, sterilized using autoclave, gamma- or ethylene oxide-sterilization, and further stored at room temperature till use.

The pH of the prepared device or dressing when dissolved in saline is preferably in the range of 6-8, depending on the hemostatic agents utilized and additives presented in the dressing.

C. Additional Materials

Optionally additional agents added to the hemostatic composition or directly to the carrier or device can include components which may be active or inert with respect to the activity of the hemostatic composition in promoting blood clotting, or may provide for an additional or different biological activity (e.g., antibacterial, anti-inflammatory, and the like).

For example, in some embodiments, inert materials that have no hemostatic effect can also be included in the content of the carrier (e.g., the dressing). Examples of inert materials are glycerin, alginate, polyacrylic acid and Carbopol®. The amount of the inert materials in the dressing is typically 1-10% of the total weight of the carrier (e.g., the dressing).

Additional active and inert agents that can be included in the hemostatic composition and/or the carrier are described in U.S. Published Application No. 2014/0255336.

Such additional agent(s) can be provided in an admixture (e.g., in dry or hydrated (e.g., solution)) with the hemostatic agent (e.g., in a slurry) or provided on the surface (e.g., for a non-porous hemostatic agent) or loaded into the hemostatic agent structure itself (e.g., for a porous hemostatic agent).

D. Exemplary Method of Making Hemostatic Composition

Dissolve Pluronics® F-127, Pluronics®F-68 or glycerol in water and stir for 2 h to prepare 1-20% (w/w) solution. Different amounts of different surfactants alone or in various combinations can used to tune to the activity of the composition. Heat the solution to 50° C. Add hemostatic agent solution (e.g. kaolin, chitosan, etc.) gradually to the previously formed solution under stirring and heating. The content of the hemostatic agent could be up to 60% of the total weight of the slurry. This slurry can also be referred to as a hemostatic composition.

Immerse the carrier or device (e.g., gauze) or spray the slurry over the gauze for full saturation. The impregnation time is usually for 5 min. The coated gauze substrate is then rolled to further embed the hemostatic agents into the material of the substrate. The gauze substrate is then dried overnight (unrolled after ca. 4 h). Binders can also be included to allow for better inclusion of the hemostatic agents into the gauze. Glycerol and chitosan are preferable binders, and they are added as indicated previously. The gauze has been rolled under high pressure, and the dust has been removed via air nozzles. Both the slurry and the final dressings are sterilized in the autoclave. For measurement of the pH, 5 cm$^2$ of the dressing is placed in 50 mL of saline. The pH is measured after 2 h. The pH values are in the range of 6-8.

Embodiments include impregnates of varying compositions, in terms of, concentrations, excipients (all are FDA approved), preparation method, and type of gauze, and other variables. As illustrated in the examples below, embodiments resulted in exceptionally high hemostatic effect.

Raw materials may be in sterile or non-sterile form, but the final products are typically sterilized using autoclave, gamma- or ethylene oxide-sterilization. Sterile water (suitable for injection) is regularly used during the preparation procedures.

II. Methods of Use

Carriers and devices treated with a disclosed hemostatic composition can be used to reduce bleeding, increase blood clotting, or a combination thereof in a subject in need thereof. The methods generally involve contacting a carrier or device treated with hemostatic composition disclosed herein to a bleeding external or internal wound or hemorrhage site of a subject for a time sufficient to reduce bleeding, promote blood clot formation, or a combination thereof.

Contact can be maintained through application of pressure, and may be held in place either by hand and/or through use of a bandage. Contact may be maintained at least until blood flow from the wound has slowed or has detectably ceased, i.e., until the wound is stabilized through formation of a clot. Once the clot is formed, the carrier or device can be removed from the wound. Where necessary, the wound can be irrigated.

These methods are applicable to a variety of different types of wounds, which may have been inflicted intentionally or through accident and at any portion of the body amenable to application of the carriers and devices, and find use in the treatment wounds of all degrees of severity ranging from bleeding skin surface wounds to wounds involving laceration of the femoral artery or other major artery or vein.

Subjects include any subject in need of treatment at an external or internal wound or hemorrhage site, and can include both human and veterinary applications (e.g., mammals such as dogs, cats, livestock (e.g., cattle, horses, sheep, goats, etc.), and the like). In some instances, the wound may include both external and internal hemorrhage sites. The wound may be a surgical wound or a trauma wound, such as, but not limited to, a surgical or traumatic soft tissue wound.

For example, the carriers and devices can be used to stop bleeding after traumatic injury, which has widespread applications for civilians in hospitals (surgery, gynecology, and many other applications) and also to save lives of soldiers in battlefield and as an essential component in the First Aid Kits.

Users of these materials should not to receive specific training for application of these dressing. Basic medical training is enough because the dressing can be applied with minimal compression for few minutes, left in the site of injury, and, thus, they can be included in the First Aid Kits.

Duration of application of the dressing on the wound, number of application times and size of the used gauze vary depending on the injury site and severity of the bleeding. Usually application of the dressing for 1-3 min on the injury site should be enough, and in, severe bleeding, it has to be tested visually until active bleeding stops.

The disclosed materials may be particularly advantageous for treating individuals with special circumstances (e.g. diabetes, hemophilia, battlefield, etc.).

III. Kits

Kits including the disclosed materials are also provided. Kits can include, for example, a hemostatic composition and a carrier or device packaged separately. In other embodiments, the kit provides a carrier or device already treated with hemostatic composition.

Embodiments of the present disclosure will be now explained with reference to the following examples, although the present disclosure is not limited to these examples.

EXAMPLES

Example 1: Nanotechnology-Based Dressings Improve In Vivo Hemostatic Efficiency in Rabbits Materials and Methods Twenty-seven adult rabbits (males and females) were purchased locally and kept at room temperature. Rabbits were kept in large cages and allowed food and water ad libitum. They were anesthetized prior to the surgical procedures using intraperitoneal thiopental injections. Rabbits were divided randomly into three groups (n=9). The first group served as a control group which received the regular dressing, the second group received a nanotechnology-based dressing, and the last group received the QUIKCLOT®.

The test embodiment was non-woven gauze impregnated with kaolin and chitosan, glycerin and Pluronic® F-127. Pluronic® F-127 nanoparticles were prepared and used to stabilize the prepared kaolin, whereas chitosan nanofibers were included in the preparation. The total amount of the hemostatic agents was ca. 50% of the total weight of the device. Pluronic was ca. 5% of the total weight of the device. Total impregnation time was 5 min.

The protocol was approved by the Assiut University Animal Ethical Committee. The animal models were developed by cutting the femoral artery and vein, and applying immediately the hemostatic agents with pressure (weight of 200 g for 3 min) and measuring the survival rates, survival durations, total amount of blood loss, time to hemostasis, and mean arterial blood pressure. No fluid resuscitation or surgical intervention was allowed during the experimental setup.

Results

This technology is based mainly on achieving prompt and efficient hemostasis via increasing the specific surface area of one or more hemostatic agents to increase the coating efficiency on the carrier (gauze, for example) and the contact with the body tissues and blood cells.

Some of the approaches utilized were to convert chitosan (an example of the hemostatic agents utilized) into micro- or nano-based fibers. It can be seen how the nanofibers have higher surface area and efficient coating on the carriers. The increase in surface areas of the various hemostatic agents used is either by converting the chitosan into chitosan microfibers or nanofibers, or by modifying the regular method of kaolin impregnation which provides inefficient coating of the dressing into better coating via the assistance of several nano-based approaches, such as, Pluronic nanoparticles or chitosan fibers. The method and conditions for producing chitosan fibers have been explained earlier.

Another example of hemostatic agents used is kaolin. The use of heated kaolin slurry in coating the non-woven gauze has been the most common method for using hemostatic dressing, with adding other binders, such as glycerin. However, this method results in low coating efficiency, which explains the relatively low hemostatic efficiency of this kind of preparations. On the contrary, the use of nanoparticles in dispersing the kaolin particles or chitosan fibers resulted in high coating efficiency on the gauzes. The method and conditions for producing efficient coating of kaolin have been explained earlier. It can be overall concluded that increasing the surface area of the hemostatic agents via the use of nano- or micro-technology-based approaches helps in improving the hemostatic efficiency of the utilized dressing.

The size of the gauze threads without any coating was 14.6±2.4 µm. The chitosan micro- and nano-based fibers had diameters of 2.4±0.9 µm and 101±56 nm, respectively. Kaolin alone and when dispersed with the assistance of Pluronic micelles had diameters of 7.9±2.2 µm and 4.7±1.9 µm, respectively. When assisted with chitosan, in the presence or absence of glycerin, they had diameters of 4.2±2.6 µm and 3.9±1.5 µm, respectively. The size of the particles of kaolin did not change that significantly, but rather their dispersibility and coating efficiency had greatly increased.

Experiments were performed by cutting the femoral artery and vein of rabbits. The femoral artery and vein in the animal model (rabbit) prior to cutting them to test the effect of the hemostatic dressings on inducing hemostasis, the amount of blood loss and the ability to maintain the normal mean arterial blood pressure were studied.

The regular dressing, QuikClot Combat Gauze, and the nanotechnology-based dressing have been applied to study the hemostasis achieved at the end of the experiment after they have been applied to stop the bleeding following cutting the femoral arteries and veins of the animal model.

The nanotechnology-based hemostatic dressing stopped the bleed faster with lower amounts of blood loss and maintained a normal mean arterial pressure, as compared to the QuikClot Combat Gauze, which was relatively more efficient in inducing the hemostasis in comparison to the regular dressing.

It can be clearly seen that the nanotechnology-based dressing had higher ability in stopping the bleeding, and in reducing the blood loss, as compared to the regular dressing and the QuikClot Combat Gauze.

Figure 2:
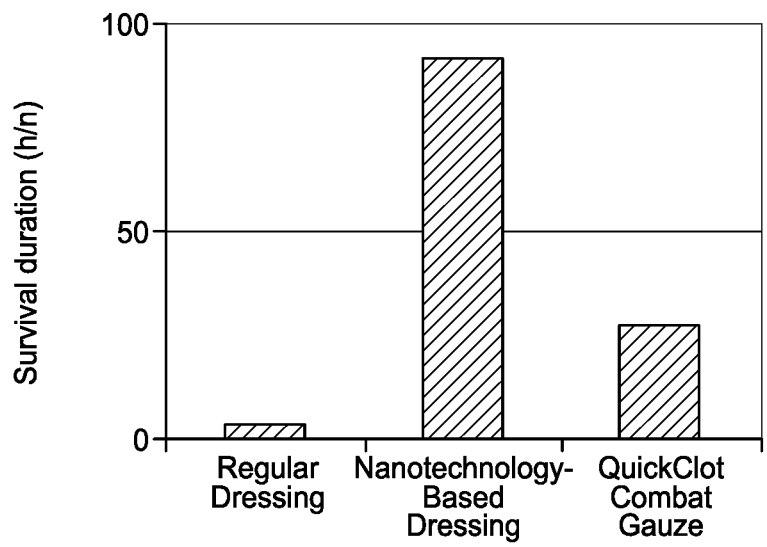
FIG. 2 is a graph displaying the mean survival durations (total number of survival hours/number of animals in each group) of animals, 1-h and 24-h, after cutting their femoral arteries and veins. Regular dressings, nanotechnology-based dressing, or QUIKCLOT® were applied immediately after injury with immediate compression for 3 min.

The nanotechnology-based dressing showed improved results, as compared to the commercial QUIKCLOT®, with exceptionally higher survival rates and lower amounts of blood losses. FIGS. 1 and 2 show the higher ability of the nanotechnology-based dressing to induce hemostasis and to improve the survival rates of the injured animals, as compared to the physical dressing or the QUIKCLOT®.

The effect of the regular dressing, QuikClot Combat Gauze and the nanotechnology-based dressing, in stopping the bleeding, reducing the blood loss, and maintaining the normal blood pressure were also observed.

At the site of femoral artery and vein injury, hemostasis has been achieved upon using the nanotechnology-based dressing, whereas higher amount of blood loss and continuous bleeding can be seen at the site of injury after utilizing the regular dressing and the QuikClot Combat Gauze, although all the experimental factors were fixed except for the type of the dressing.

FIG. 1 shows the percentage of survival of animals, 1-h and 24-h, after cutting their femoral arteries and veins. Regular dressings, nanotechnology-based dressing, or QUIKCLOT® were applied immediately after injury with immediate compression for 3 min.

FIG. 2 shows the mean survival durations (total number of survival hours/number of animals in each group) of animals, 1-h and 24-h, after cutting their femoral arteries and veins. Regular dressings, nanotechnology-based dressing, or QUIKCLOT® were applied immediately after injury with immediate compression for 3 min.

Figure 3:
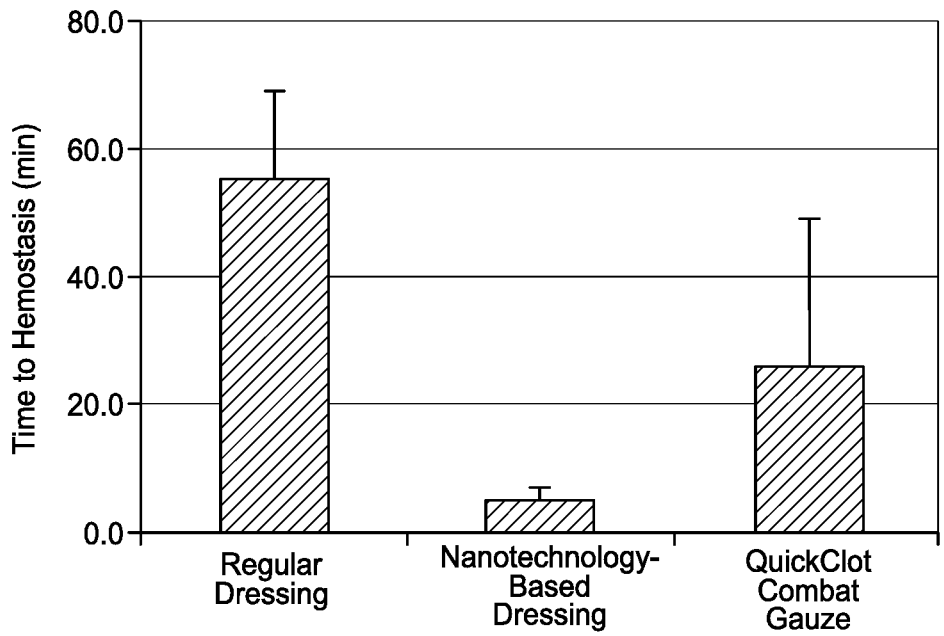
FIG. 3 is a graph displaying the total time to hemostasis of animals after cutting their femoral arteries and veins. Regular dressing, nanotechnology-based dressing, and QUIKCLOT® were applied immediately after injury with immediate compression for 3 min. The measurements were performed over one hour and the animals that died were assigned time to hemostasis of 60 min.

FIG. 3 shows the total time to hemostasis of animals after cutting their femoral arteries and veins. Regular dressing, nanotechnology-based dressing, and QUIKCLOT® were applied immediately after injury with immediate compression for 3 min. The measurements were performed over one hour and the animals died were assigned time to hemostasis of 60 min.

Figure 4:
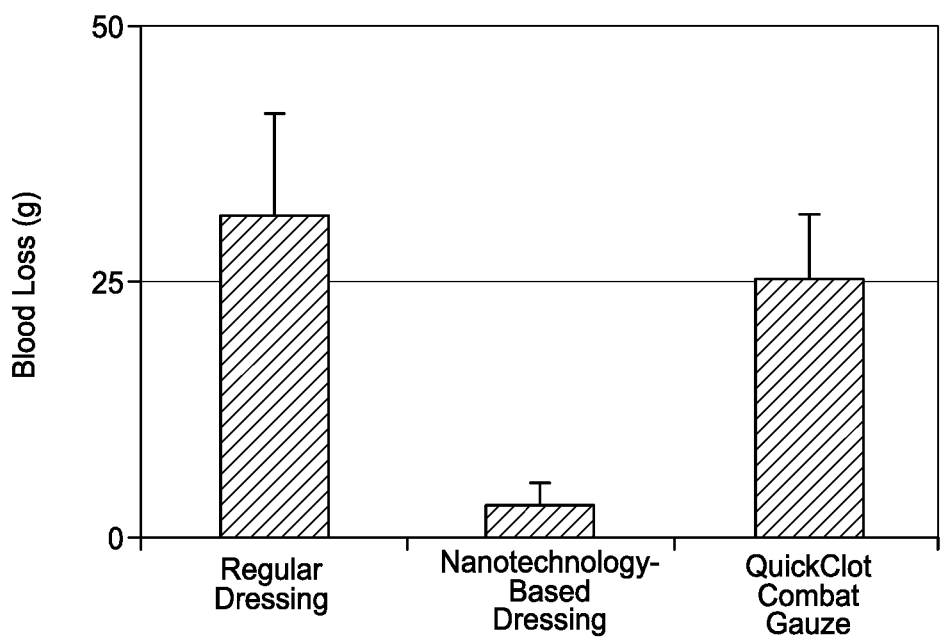
FIG. 4 is a graph displaying the total amounts of blood loss of animals after cutting their femoral arteries and veins. Regular dressing, nanotechnology-based dressing, and QUIKCLOT® were applied immediately after injury with immediate compression for 3 min. Leaked blood was absorbed by regular gauze and the differences in the total weight of all the used gauze before and after the experiments were calculated.

FIG. 4 shows the total amounts of blood loss of animals after cutting their femoral arteries and veins. Regular dressing, nanotechnology-based dressing, and QUIKCLOT® were applied immediately after injury with immediate compression for 3 min. Leaked blood was absorbed by regular gauze and the differences in the total weight of all the used gauze before and after the experiments were calculated.

Figure 5:
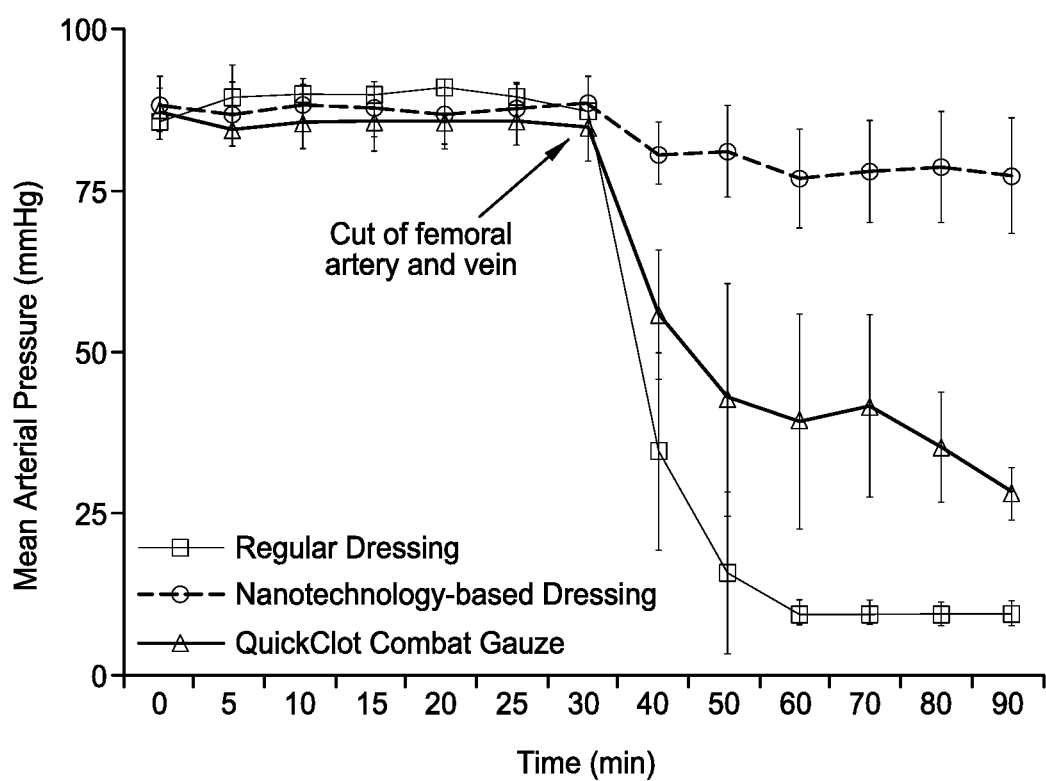
FIG. 5 is a graph displaying the mean arterial pressure of the animals after cutting their femoral arteries and veins. Regular dressing, nanotechnology-based dressing, and QUIKCLOT® were applied immediately after injury with immediate compression for 3 min. The measurements over the first 30 min represent the mean arterial pressure of animals before cutting their femoral arteries and veins.

FIG. 5 shows the mean arterial pressure of the animals after cutting their femoral arteries and veins. Regular dressing, nanotechnology-based dressing, and QUIKCLOT® were applied immediately after injury with immediate compression for 3 min. The measurements over the first 30 min represent the mean arterial pressure of animals before cutting their femoral arteries and veins.

Example 2: Nanotechnology-Based Dressings Improve In Vivo Hemostatic Efficiency in Humans Materials and Methods The materials and methods of making were the same as for the previous animal experiment in Example 1.

Based on the promising results of the experimental trials, a protocol for clinical assessment was established aiming at assessing the use of nanotechnology-based dressings on human subjects for controlling of bleeding from either external wounds (EX) or intra-corporeal wound (abdominal cavity, IC). The main goals were to evaluate the safety and efficacy of the nanotechnology-based dressings.

The protocol was approved by the "Ethical Committee" of Assiut University Faculty of Medicine. An informed consent was obtained from all the included subjects. The subjects were patients undergoing different types of surgeries that may lead to bleeding during the steps of the operation. The bleeding surfaces could be external (EX) or intra-corporeal (IC).

The bleeding was classified according to its severity into:
1. Mild: Where it is possible to stop the bleeding by normal-gauze compression.
2. Moderate: Where it is possible to stop the bleeding by electric cautery (diathermy).
3. Severe: Where it is only possible to stop the bleeding by suturing and/or ligation.

Excluded from the trials are extensive bleeding points that appeared to result from significant arterial injuries (these were already tested in animals but unethical to be tested in human). For each included case, the following criteria were collected, evaluated, or characterized: demographic data; type of operation; type of bleeding surface; severity of bleeding; size and folds of the gauze used; number of applications; total time of application; effects of application of the described embodiment are categorized into the following four categories:

Poor: Bleeding persisted and another hemostatic method was applied.

Fair: Bleeding decreased but another method was still applied.

Good: Minor bleeding persisted but there was no need for further hemostasis.

Excellent: Bleeding stopped completely.

Any related complications, whether intra- or post-operative, were reported.

Results

Based on the promising results of the experimental trials, a protocol for clinical assessment was established aiming at assessing the use of nanotechnology-based dressings on human subjects for controlling of bleeding from either external wounds (EX) or intra-corporeal wound (abdominal cavity, IC). The main goals were to evaluate the safety and efficacy of the nanotechnology-based dressings.

Nanotechnology-based dressings were tested for their abilities to stop bleeding during several surgical procedures. Significant differences as compared to the regular physical dressings were observed. The new dressing succeeded to stop bleeding in cases where the regular physical dressing, and sometimes, even the electric cautery, had failed to do so. No complications have been found in those patients related to the use of the new dressing.

Twenty three (23) patients were included in the clinical trial. Nanotechnology-based dressings were applied to all of them.

Case 1:
36 years old male
Inguinal mesh Hernioplasty
Bleeding surface: EX, subcutaneous tissue
Moderate bleeding
12×20 cm$^2$—in 4 folds
One application
4 min
Excellent results
No complications Case 2
45 years old female
Recurrent incisional Hernioplasty
Bleeding surface: EX, subcutaneous tissue
Moderate bleeding
12×40 cm$^2$—in 4 folds
One application
4 min
Good results
No complications Case 3:
22 years old male
Inguinal mesh Hernioplasty
Bleeding surface: EX, subcutaneous tissue
Moderate bleeding
12×20 cm$^2$—in 4 folds
One application
4 min
Excellent results
No complications Case 4:
41 years old female
Laparoscopic cholecystectomy
Bleeding surface: IC, liver surface (gall bladder bed)
Moderate bleeding
8×40 cm$^2$—in 4 folds
One application
4 min
Excellent results
No complications Case 5:
55 years old female
Laparoscopic cholecystectomy
Bleeding surface: IC, liver surface (gall bladder bed)
Moderate bleeding
8×40 cm$^2$—in 4 folds
Two applications
8 min
Excellent results
No complications Case 6:
38 years old male
Open cholecystectomy for gangrenous cholecystitis
Bleeding surface: IC, liver surface (gall bladder bed)
Severe bleeding
12×40 cm$^2$—in 4 folds
Two applications
8 min
Excellent results
No complications Case 7:
33 years old female
Laparoscopic cholecystectomy
Bleeding surface: IC, liver surface (gall bladder bed)
Moderate bleeding
8×40 cm$^2$—in 4 folds
One application 4 min
Excellent results
No complications
Case 8:
48 years old female
Laparoscopic cholecystectomy
Bleeding surface: IC, liver surface (gall bladder bed)
Severe bleeding (with venous sinuses, failed cautery)
8×40 cm² — in 4 folds
Two applications
8 min
Excellent results
No complications
Case 9:
62 years old female
Laparoscopic cholecystectomy
Bleeding surface: IC, internal peritoneal surface at the umbilical port
Moderate bleeding
8×20 cm² — in 4 folds
One application
4 min
Excellent results
No complications
Case 10:
38 years old female
Open appendectomy
Bleeding surface: site of dissection, sub-hepatic retroperitoneal tissue, inaccessible to cautery
Moderate bleeding
12×80 cm² — in 4 folds
One application
4 min
Excellent results
No complications
Case 11:
48 years old male
Open appendectomy
Bleeding surface: site of dissection of retrocecal appendicular mass
12×80 cm² — in 4 folds
One application
4 min
Good results
No complications
Case 12:
65 years old female
Laparoscopic cholecystectomy
Bleeding surface: IC, internal peritoneal surface at the umbilical port
Moderate bleeding
12×20 cm² — in 4 folds
Two applications
8 min
Fair results: bleeding stopped except for an arterial bleeder that needed cautery
No complications
Case 13:
58 years old female
Open cholecystectomy for pyocele of the gall bladder
Bleeding surface: IC, liver surface (gall bladder bed)
Severe bleeding
12×40 cm² — in 4 folds
One application
20 min
Excellent results
No complications
Case 14:
57 years old female
Laparoscopic cholecystectomy
Bleeding surface: IC, liver surface (gall bladder bed)
Severe bleeding (with venous sinuses, failed cautery and would be difficult for suturing due to fear of lacerated liver tissue during suturing)
8×40 cm² — in 4 folds
Two applications
8 min
Excellent results
No complications
Case 15:
62 years old female
Open cholecystectomy for pyocele of the gall bladder
Bleeding surface: IC, liver surface (gall bladder bed)
Severe bleeding
12×40 cm² — in 4 folds
One application
20 min
Excellent results
No complications
Case 16:
43 years old female
Laparoscopic cholecystectomy
Bleeding surface: IC, trocar injury of the liver
Severe bleeding: failed electric cautery
6×4 cm² — in 4 folds
One application
4 min
Excellent
No complications
Case 17:
39 years old male
Open cholecystectomy for huge pyocele of the gall bladder
Bleeding surface: IC, liver surface (gall bladder bed)
Severe bleeding
12×40 cm² — in 4 folds
One application
20 min
Good results: minor bleeding at the edge persists without the need for further hemostasis
No complications
Case 18:
50 years old male
Laparoscopic cholecystectomy
Bleeding surface: IC, liver surface (gall bladder bed)
Severe bleeding: failed electric cautery
8×20 cm² — in 4 folds
One application
4 min
Excellent results
No complications
Case 19:
74 years old female
Laparoscopic cholecystectomy
Bleeding surface: IC, liver surface (gall bladder bed)
Severe bleeding: failed electric cautery
8×20 cm² — in 4 folds
One application
4 min
Excellent results
No complications Case 20:
50 years old male
Heamorrhoidectomy: removed large primary piles and cauterized large daughter piles
Bleeding surface: EX, surface ooze
Moderate bleeding
12×20 cm² — in 4 folds
One application
4 min
Excellent
No complications Case 21:
55 years old male
Perianal fistula: fistulectomy
Bleeding surface: EX, surface ooze
moderate bleeding
12×20 cm² — in 4 folds
One application
4 min
Good results: minor bleeding persisted at the edge of the wound without the need for further hemostasis
No complications Case 22:
43 years old male
Heamorrhoidectomy: removed large primary piles and cauterized large daughter piles
Bleeding surface: EX, surface ooze
Moderate bleeding
12×20 cm² — in 4 folds
One application
4 min
Fair results: minor bleeding persisted at the edge of the wound that needed minor electric cautery
No complications Case 23:
28 years old female
Laparoscopic cholecystectomy
Bleeding surface: IC, liver surface (gall bladder bed)
Severe bleeding: failed cautery
8×20 cm² — in 4 folds
One application
4 min
Excellent results
No complications Table 1 shows the data summary for the results of the clinical cases.

TABLE 1

| Case No. | Sex | Age | Operation | Bleeding Surface | *Severity of bleeding | Size and folds of gauze | Applications: number and total time | **Effect | Complications |
|---|---|---|---|---|---|---|---|---|---|
| 1 | M | 36 | Inguinal hernioplasty | Subcutaneous tissue | Moderate | 12 × 20 cm² - 4 folds | One - 8 min | Excellent | None |
| 2 | F | 45 | Incisional hernioplasty | Subcutaneous tissue | Moderate | 12 × 40 cm² - 4 folds | One - 4 min | Good | None |
| 3 | M | 22 | Inguinal hernioplasty | Subcutaneous tissue | Moderate | 12 × 20 cm² - 4 folds | One - 4 min | Excellent | None |
| 4 | F | 51 | Laparoscopic cholecystectomy | Liver surface | Moderate | 8 × 40 cm² - 4 folds | One - 4 min | Excellent | None |
| 5 | F | 55 | Laparoscopic cholecystectomy | Liver surface | Moderate | 8 × 40 cm² - 4 folds | Two - 8 min | Excellent | None |
| 6 | M | 38 | Open cholecystectomy | Liver surface | Severe | 12 × 40 cm² - 4 folds | Two - 8 min | Excellent | None |
| 7 | F | 33 | Laparoscopic cholecystectomy | Liver surface | Moderate | 8 × 40 cm² - 4 folds | One - 4 min | Excellent | None |
| 8 | F | 48 | Laparoscopic cholecystectomy | Liver surface | Severe (venous sinuses) | 8 × 40 cm² - 4 folds | Two - 8 min | Excellent | None |
| 9 | F | 62 | Laparoscopic cholecystectomy | Umbilical peritoneum | Moderate | 8 × 20 cm² - 4 folds | One - 4 min | Excellent | None |
| 10 | F | 38 | Appendectomy | Retroperitoneal tissue | Moderate | 8 × 80 cm² - 4 folds | One - 4 min | Excellent | None |
| 11 | M | 48 | Appendectomy | Retroperitoneal tissue | Moderate | 8 × 80 cm² - 4 folds | One - 4 min | Good | None |
| 12 | F | 65 | Laparoscopic cholecystectomy | Umbilical peritoneum | Moderate | 8 × 20 cm² - 4 folds | Two - 8 min | Fair | None |
| 13 | F | 58 | Open cholecystectomy | Liver surface | Severe | 8 × 40 cm² - 4 folds | One - 20 min | Excellent | None |
| 14 | F | 57 | Laparoscopic cholecystectomy | Liver surface | Severe (venous sinuses) | 8 × 40 cm² - 4 folds | Two - 8 min | Excellent | None |
| 15 | F | 62 | Open cholecystectomy | Liver surface | Severe | 8 × 40 cm² - 4 folds | One - 20 min | Excellent | None |
| 16 | F | 43 | Laparoscopic cholecystectomy | Liver tissue | Severe | 6 × 4 cm² - 4 folds | One - 4 min | Excellent | None |
| 17 | M | 39 | Open cholecystectomy | Liver surface | Severe | 8 × 40 cm² - 4 folds | One - 20 min | Good | None |
| 18 | M | 50 | Laparoscopic cholecystectomy | Liver surface | Severe | 8 × 20 cm² - 4 folds | One - 4 min | Excellent | None |
| 19 | F | 74 | Laparoscopic cholecystectomy | Liver surface | Severe | 8 × 20 cm² - 4 folds | One - 4 min | Excellent | None |
| 20 | M | 50 | Heamorrhoidectomy | Subcutaneous and submucosal tissue | Moderate | 12 × 20 cm² - 4 folds | One - 4 min | Excellent | None |
| 21 | M | 55 | Perianal fistulectomy | Subcutaneous tissue | Moderate | 12 × 20 cm² - 4 folds | One - 4 min | Good | None |

TABLE 1-continued

| Case No. | Sex | Age | Operation | Bleeding Surface | *Severity of bleeding | Size and folds of gauze | Applications: number and total time | **Effect | Complications |
|---|---|---|---|---|---|---|---|---|---|
| 22 | M | 43 | Heamorrhoidectomy | Subcutaneous and submucosal tissue | Moderate | 12 × 20 cm² - 4 folds | One - 4 min | Fair | None |
| 23 | F | 28 | Laparoscopic cholecystectomy | Liver surface | Severe | 8 × 40 cm² - 4 folds | One - 4 min | Excellent | None |

With respect to Table 1:
*Bleeding severity: Mild: It is possible to stop the bleeding by normal-gauze compression; Moderate: It is possible to stop the bleeding by electric cautery (diathermy); Severe: It is possible to stop the bleeding only by suturing and/or ligation.
**Effect of application: Poor: Bleeding persisted and another hemostatic method had to be applied; Fair: Bleeding decreased but another method still needed to be applied; Good: Minor bleeding persisted but there was no need for further hemostasis; Excellent: Bleeding stopped completely.

Twenty three cases were included in the study including 14 females and 9 males with a mean age of 45.7 years (ranging from 22 to 74 years old). Different types of operations were performed, namely, 3 hernias, 15 cholecystectomies, 2 appendectomies, 2 heamorrhoidectomies, and one perianal fistulectomy. Additionally, different types of bleeding tissue surfaces were included as subcutaneous tissues, liver surface, peritoneal surface, submucosal tissues, and retroperitoneal tissues. All these data shows the diversity of circumstances in which nanotechnology-based dressings were utilized, e.g., different age, sex, operation type, and bleeding tissue surface.

Regarding the bleeding severity, 13 cases had moderate bleeding that usually would have needed electric cautery for hemostasis and 10 cases had severe bleeding that usually would have needed suturing for hemostasis with the possibility of tissue laceration with exaggerated bleeding in four of them during suturing (cases 8, 14, 15 and 19 with friable liver tissue).

Regarding the surface area used of the nanotechnology-based dressings, the width ranged from 6 to 12 cm and the length ranged from 4 to 80 cm. All the patches were folded into 4 layers. This size and shape proved to be easy to use even through surgical ports of laparoscopic surgery.

For each patient, the nanotechnology-based dressing was used for one or two applications with a total application time that ranged mostly from 4 to 20 min.

This application time seemed short enough not to significantly affect the total operative time of procedures like hernioplasty or cholecystectomy. Even in the three cases that the application time reached 20 min, other operative steps were possible to be performed in the meanwhile and the total operative time ranged from 110 to 140 min without significant time elongation due to the application.

The hemostatic effect of the nanotechnology-based dressings was stated as "excellent" in 17 cases (73.9%), "good" in 4 cases (17.4%), "fair" in two cases (8.7%), and no cases with "poor" effect. The excellent effect means complete stoppage of bleeding with no need for further hemostasis. The nanotechnology-based dressing showed "excellent" effect in 9 out of the 10 cases with severe bleeding. Two of those cases with severe bleeding had venous sinus bleeding from the liver surface for which cautery failed to stop the bleeding and suturing would have caused laceration of the liver tissues. Moreover, in cases of laparoscopic procedures, suturing is difficult and lengthy procedure. The use of the nanotechnology-based dressing in those two cases stopped the bleeding completely without suturing.

The nanotechnology-based dressing demonstrated "good" effect in four patients. One of them had incisional hernia and needed extensive dissection of the abdominal wall. In spite of the persistent minor bleeding, there was no need for further hemostasis after the use of nanotechnology-based dressing. The second patient had appendectomy where the bleeding site was subhepatic retroperitoneal tissues. From a classic appendectomy incision, this site is partially inaccessible for cautery hemostasis. The application of the nanotechnology-based dressing showed "good" effect with minor persistent bleeding that needed no further hemostasis. The third patient had severe bleeding with "good" hemostatic effect using the new dressing. He had open cholecystectomy with bleeding from a wide area of the gall bladder bed. Only minor bleeding persisted at the edge of the bleeding area that needed no further hemostasis. The fourth patient had perianal fistulectomy for both anterior and posterior fistulae with moderate ooze from the wound. Application of the new dressing left minor bleeding at the edges that needed no further hemostasis. For the results of the last two cases, the explanation could be on the basis that the edges of the bleeding surface could have lower contact with the dressing than the central area during the application.

Two cases had "fair" results with the use of the nanotechnology-based dressing. One patient had bleeding from the umbilical peritoneal surface at the site of one of the laparoscopic incisions. The application caused cessation of bleeding except for an arterial spurter. Due to the difficult accessibility to the bleeding site, cautery was used to stop the bleeding. The other patient had third degree bleeding piles with large primary and daughter piles. The application of the new dressing had "fair" results with minor submucosal bleeding that needed minor electric cautery to stop it. Hemorrhoidectomy for bleeding piles required strict hemostasis to avoid any post-operative bleeding attacks. Hence, we preferred to use electric cautery to stop this minor bleeding remnant completely.

On the other hand, no cases with "poor" effect were encountered using the nanotechnology-based dressing.

No complications related to the use of the nanotechnology-based dressing were recorded, whether locally at the sites of applications or generally for the patient as a whole. Additionally, all the patients were followed for at least one month after the operations with no reported related complications.

These clinical data demonstrate that this nanotechnology-based dressing is an effective tool in controlling different types of bleeding tissue surfaces with acceptable efficiency and high safety profile. It could be added to the surgical tools to stop bleeding during operations.

Unless defined otherwise, all technical and scientific terms used herein have the same meanings as commonly understood by one of skill in the art to which the disclosure belongs. Publications cited herein and the materials for which they are cited are specifically incorporated by reference.

Those skilled in the art will recognize, or be able to ascertain using no more than routine experimentation, equivalents to the specific embodiments described herein, which are encompassed by the following claims.

We claim:

1. A hemostatic composition comprising:
   two hemostatic agents comprising kaolin and chitosan, wherein:
      a total amount of hemostatic agents is about 50 wt % of a total weight of the hemostatic composition;
      at least one of the hemostatic agents is in a form having a dimension less than 1 micron;
      a first portion of the chitosan is in a form of nanofibers;
      a second portion of the chitosan is in a form of microfibers; and
      the chitosan microfibers and chitosan nanofibers have diameters of 2.4±0.9 μm and 101±56 nm, respectively;
   a carrier or a device comprising non-woven gauze;
   glycerin; and
   a surfactant comprising Pluronic F-127, wherein:
      the Pluronic F-127 is in a form of nanoparticles as a micelle;
      the Pluronic F-127 is configured to stabilize the kaolin; and
      an amount of Pluronic F-127 in the hemostatic composition is between 0.5 wt % and 5 wt % of the total weight of the hemostatic composition;
   wherein the kaolin dispersed with assistance of the Pluronic F-127 micelles has a diameter of 4.7±1.9 μm;
   wherein the non-woven gauze is impregnated with the hemostatic agents, the surfactant, and the glycerin;
   wherein the hemostatic agents are in combination with the surfactant in an effective amount to reduce bleeding, increase clotting, or a combination thereof when applied to the non-woven gauze and contacted with a wound or hemorrhage on a subject; and
   wherein the surfactant is present in an effective amount to increase stability, enhance disbursement, or increase a surface area of one of the two hemostatic agents.

2. The hemostatic composition of claim 1, further comprising oxidized regenerated cellulose, collagen, or a combination thereof.

3. The hemostatic composition of claim 1, wherein the hemostatic composition is characterized (rabbit model) as having a time to hemostasis of less than 20 minutes after applying the hemostatic composition to an injury.

4. The hemostatic composition of claim 1, wherein the hemostatic composition is characterized (rabbit model) as having a total amount of blood loss of less than 25 grams after applying the hemostatic composition to an injury.

5. The hemostatic composition of claim 1, wherein the chitosan is in the form of nanofibers formed by electrospinning.

6. The hemostatic composition of claim 1, wherein the carrier or the device is degradable.

7. The hemostatic composition of claim 1, wherein the carrier or the device is non-degradable.

8. The hemostatic composition of claim 1, wherein the total amount of the Pluronic F-127 is about 5% of the total weight of the hemostatic composition.

9. The hemostatic composition of claim 1, wherein the kaolin alone has a diameter of 7.9±2.2 μm.

10. A hemostatic composition comprising:
    two hemostatic agents comprising kaolin and chitosan, wherein:
       a total amount of hemostatic agents is about 50 wt % of a total weight of the hemostatic composition;
       at least one of the hemostatic agents is in a form having a dimension less than 1 micron;
       a first portion of the chitosan is in a form of nanofibers, the chitosan nanofibers having a diameter of 101±56 nm; and
       a second portion of the chitosan is in a form of microfibers, the chitosan microfibers having a diameter of 2.4±0.9 μm;
    non-woven gauze;
    glycerin; and
    a surfactant comprising Pluronic F-127, wherein:
       the Pluronic F-127 is in a form of nanoparticles as a micelle;
       the Pluronic F-127 is configured to stabilize the kaolin; and
       an amount of Pluronic F-127 in the hemostatic composition is about 5 wt % of the total weight of the hemostatic composition,
    wherein the kaolin alone has a diameter of 7.9±2.2 μm;
    wherein the kaolin dispersed with assistance of the Pluronic F-127 micelles has a diameter of 4.7±1.9 μm;
    wherein the non-woven gauze is impregnated with the hemostatic agents, the surfactant, and the glycerin;
    wherein the hemostatic agents are in combination with the surfactant in an effective amount to reduce bleeding, increase clotting, or a combination thereof when applied to the non-woven gauze and contacted with a wound or hemorrhage on a subject; and
    wherein the surfactant is present in an effective amount to increase stability, enhance disbursement, or increase a surface area of one of the two hemostatic agents.

11. The hemostatic composition of claim 10, further comprising oxidized regenerated cellulose, collagen, or a combination thereof.

12. The hemostatic composition of claim 10, wherein the hemostatic composition is characterized (rabbit model) as having a time to hemostasis of less than 20 minutes after applying the hemostatic composition to an injury.

13. The hemostatic composition of claim 10, wherein the hemostatic composition is characterized (rabbit model) as having a total amount of blood loss of less than 25 grams after applying the hemostatic composition to an injury.

14. The hemostatic composition of claim 10, wherein the chitosan is in the form of nanofibers formed by electrospinning.

15. The hemostatic composition of claim 10, wherein the carrier or the device is degradable.

16. The hemostatic composition of claim 10, wherein the carrier or the device is non-degradable.

* * * * *